US007722556B2

(12) United States Patent
Warner (10) Patent No.: US 7,722,556 B2
(45) Date of Patent: May 25, 2010

(54) ANKLE FOOT ORTHOSIS AND METHOD THEREFOR

(76) Inventor: Mitchell S. Warner, 2578 Balcastro St., Suite 101, Las Vegas, NV (US) 89117

( * ) Notice: Subject to any disclaimer, the term of this patent is extended or adjusted under 35 U.S.C. 154(b) by 138 days.

(21) Appl. No.: 11/874,483

(22) Filed: Oct. 18, 2007

(65) Prior Publication Data

US 2009/0105624 A1  Apr. 23, 2009

(51) Int. Cl.
*A61F 5/00* (2006.01)
(52) U.S. Cl. .......................................... 602/23; 602/27
(58) Field of Classification Search ............. 602/26–30, 602/60–62; 128/882
See application file for complete search history.

(56) References Cited

U.S. PATENT DOCUMENTS 5,219,324 A * 6/1993 Hall ............................ 602/28
5,897,515 A * 4/1999 Willner et al. ................ 602/27
D503,480 S    3/2005 Ingimundarson et al.
6,945,947 B2  9/2005 Ingimundarson et al.
7,063,727 B2  6/2006 Phillips et al.
2001/0031935 A1* 10/2001 Andersen ..................... 602/23
2004/0102727 A1*  5/2004 Smits .......................... 602/28

FOREIGN PATENT DOCUMENTS

GB           2168610 A  *  6/1986

* cited by examiner

*Primary Examiner*—Michael A. Brown
(74) *Attorney, Agent, or Firm*—Veronica-Adele R. Cao; Weiss & Moy, P.C.

(57) ABSTRACT

An ankle foot orthosis that provides a patient with forward flexing, energy loading, and balance control. The orthosis may also be adjustable for size and fit. The orthosis couples opposing stabilization forces that help to provide optimal balance control.

10 Claims, 10 Drawing Sheets

ANKLE FOOT ORTHOSIS AND METHOD THEREFOR

FIELD OF THE INVENTION

This invention relates generally to orthopedic devices and, more specifically, to an ankle foot orthosis and method therefor.

BACKGROUND OF THE INVENTION

Drop Foot or Foot Drop is an abnormal neuromuscular disorder that affects a patient's ability to raise his/her foot at the ankle. A patient experiencing Drop Foot will also be unable to point his/her toes toward the body (dorsiflexion) or move the foot at the ankle inward or outward. The loss of function may also be accompanied by pain, weakness, and numbness.

Drop Foot makes walking difficult, causing a person to either drag the foot and toes or to engage in a high-stepping walk called "steppage gait." The condition is not a disease, but a symptom of an underlying problem. It is often caused by an interruption in the signal from the brain to the peroneal nerve. This nerve runs along the outside of the lower leg below the knee. People with amyotrophic lateral sclerosis (ALS), multiple sclerosis (MS), Parkinson's Disease, spinal cord injuries, traumatic brain injuries, cerebral palsy, and stroke may experience the effects of the condition.

The underlying cause of the patient's Drop Foot is what dictates the type of treatment to be used. Some patients may be fitted with an Ankle Foot Orthosis (AFO), brace, or splint that fits into the shoe to stabilize the ankle/foot. Currently used ankle foot orthosis designs have side struts, but none of these devices provide forward flexing, energy loading, or balance control. Therefore, a need exists for an ankle foot orthosis that provides a patient with forward flexing, energy loading, and balance control.

SUMMARY OF THE INVENTION

It is an object of the present invention to provide an ankle foot orthosis that provides a patient with forward flexing.

It is another object of the present invention to provide an ankle foot orthosis that has an energy loading/storing function.

It is another object of the present invention to provide an ankle foot orthosis that provides a patient with balance control.

BRIEF DESCRIPTION OF THE PREFERRED EMBODIMENTS

In accordance with one embodiment of the present invention, an ankle foot orthosis is disclosed. The orthosis comprises a concave front support member, a concave middle support member extending from a distal end of the front support member, a rear support member extending from a distal end of the middle support member, and a foot plate extending perpendicularly from a distal end of the rear support member.

In accordance with another embodiment of the present invention, an ankle foot orthosis is disclosed. The ankle foot orthosis comprises a concave front support member that defines an oval aperture dimensioned to frame the anterior surface of the tibia of a user, a concave middle support member extending from a distal end of the front support member, a rear support member extending from a distal end of the middle support member, the rear support member being dimensioned to contact the back of the calf muscle of a user, and a foot plate extending perpendicularly from a distal end of the rear support member.

In accordance with another embodiment of the present invention, a method for providing balance control is disclosed. The method comprises the step of providing an ankle foot orthosis comprising a concave front support member, a concave middle support member extending from a distal end of the front support member, a rear support member extending from a distal end of the middle support member, and a foot plate extending perpendicularly from a distal end of the rear support member. The method further comprises the steps of providing lateral stabilization by side portions of the front support member, providing forward stabilization by a proximal end and the distal end of the front support member, and providing rear stabilization by the rear support member.

The foregoing and other objects, features, and advantages of the present invention will be apparent from the following, more particular description of the preferred embodiments of the invention, as illustrated in the accompanying drawings.

DETAILED DESCRIPTION OF THE PREFERRED EMBODIMENTS

The novel features believed characteristic of the invention are set forth in the appended claims. The invention will best be understood by reference to the following detailed description of illustrated embodiments when read in conjunction with the accompanying drawings, wherein like reference numerals and symbols represent like elements.

FIGS. 1-17 disclose an ankle foot orthosis, hereinafter referred to as orthosis 10. The orthosis 10 comprises a front support member 12, a middle support member 24, a rear support member 28, and a foot plate 30.

The front support member 12 is shown as being concave to receive the anterior portion 51 of the leg 50 below the knee 56. The front support member 12 defines an aperture 16 that is dimensioned to frame the anterior surface of the tibia (not shown) of a user. This aperture 16 is oval in shape and helps to prevent pressure buildup on the anterior surface of the tibia. While it is preferred that the front support member 12 define the aperture 16, it should be clearly understood that substantial benefit may be derived from the aperture 16 having a different shape, as long as the aperture 16 relieves pressure from the anterior surface of the tibia. It should also be understood that substantial benefit may nevertheless be derived from the front support member 12 having no aperture 16.

Referring to FIGS. 1-9, the front support member 12 has side portions 18 that provide lateral stabilization to the leg 50 of the user. And forward stabilization is provided by a proximal end 20 and the distal end 14 of the front support member 12. As shown in FIGS. 10-17, the distal end 14 of the front support member 12 may have means for adjusting its size. The distal end 14 may have two buckles 15, wherein one buckle 15 is attached to a distal end 19 of each of the two side portions 18 of the front support member 12. There will also be an adjustable strap 21 coupled to the two buckles 15. By tightening or loosening the adjustable strap 21, the two side portions 18 contract or relax, respectively, thereby altering the shape of the front support member 12 to better fit the leg 50 of the user. It should be clearly understood, however, that further substantial benefit may be derived from using alternative adjustment means.

The middle support member 24 extends from the distal end 14 of the front support member 12. The middle support member 24 is concave to receive either a lateral portion 52 or a medial portion 54 of the user's leg 50, as the orthosis 10 may be used with a right or left leg 50 interchangeably. It should be clearly understood, however, that substantial benefit may be derived from the orthosis 10 being made specifically for a right or specifically for a left leg.

The rear support member 28 extends from a distal end 26 of the middle support member 24. The rear support member 28 is shown as being flat to receive the back of the calf muscle 48 of the user. By coupling the distal end 14 of the front support member 12 to a proximal end 27 of the rear support member 28, via the middle support member 24, a force couple is created. This coupling of opposing stabilization forces, i.e. forward stabilization force (exerted by the front support member 12) coupled with rear stabilization force (exerted by the rear support member 28), helps to provide balance stabilization to the leg 50 of the user.

Figure 1:
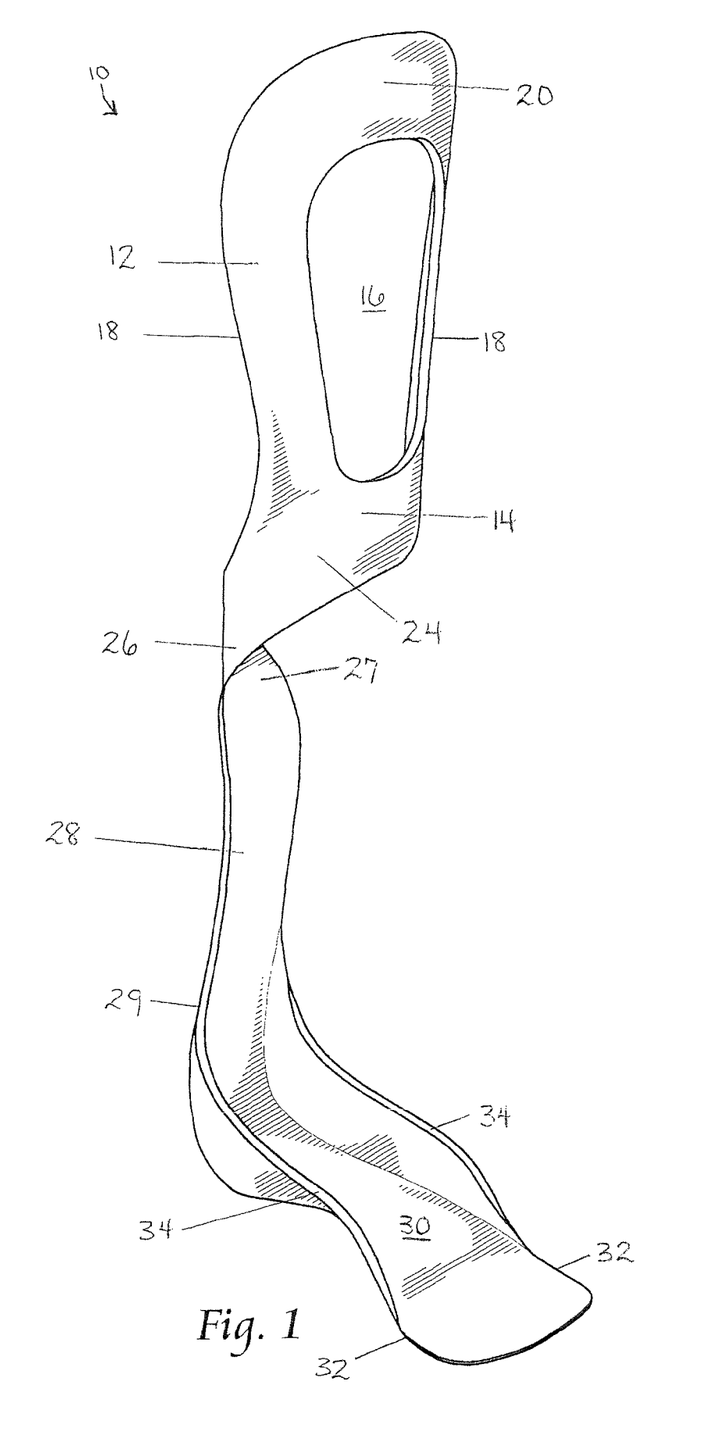
FIG. 1 is perspective view of an embodiment of an ankle foot orthosis of the present invention.
Figures 2, 3:
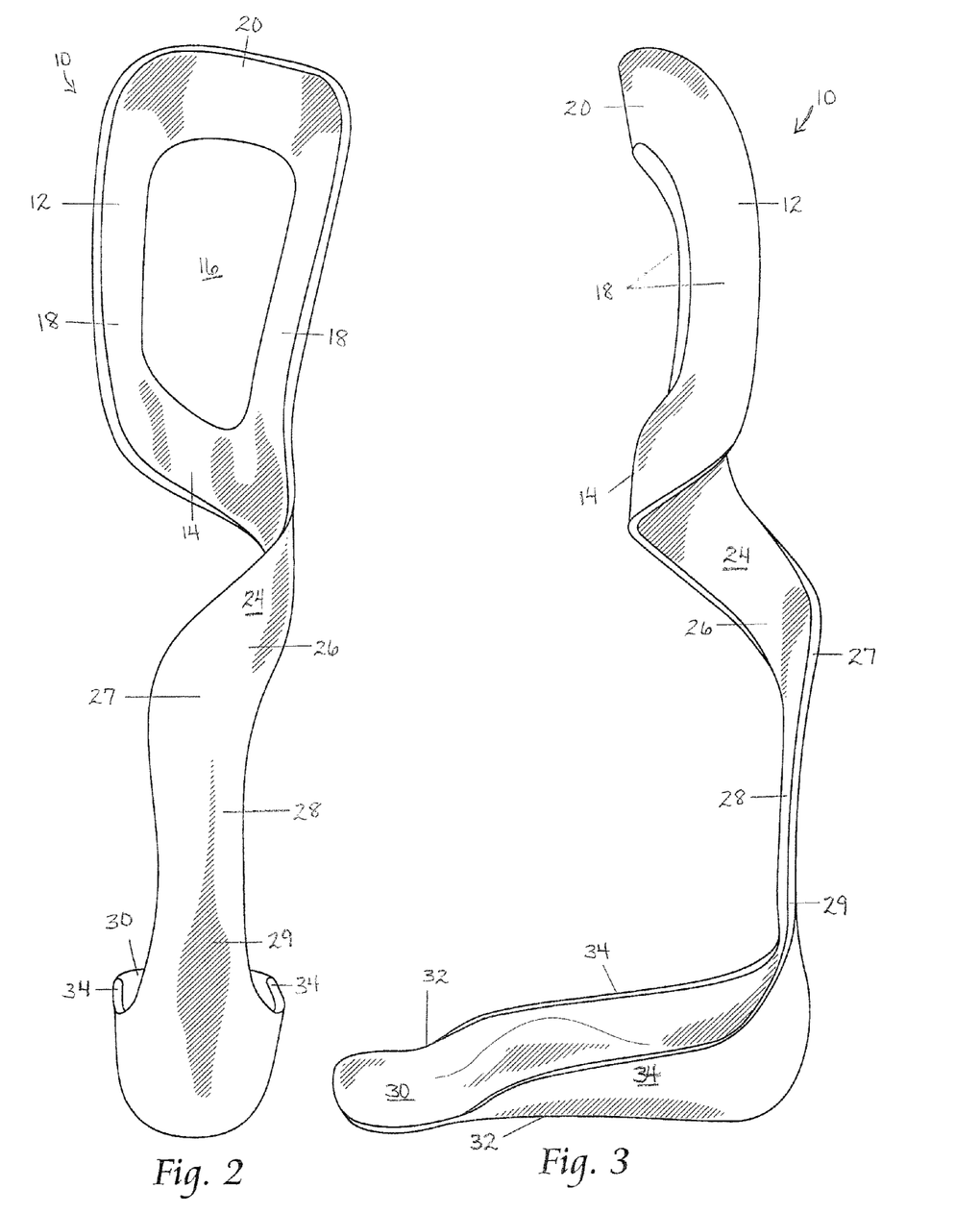
FIG. 2 is a rear view of the orthosis of FIG. 1.
FIG. 3 is a left side view of the orthosis of FIG. 1.
Figure 4:
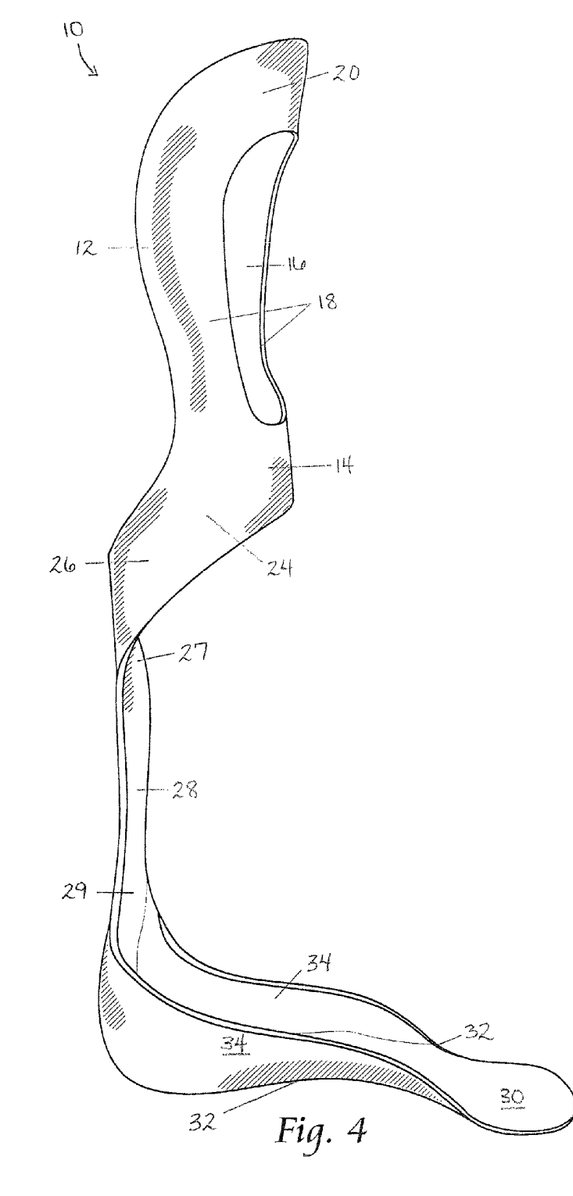
FIG. 4 is a right side view of the orthosis of FIG. 1.
Figure 5:
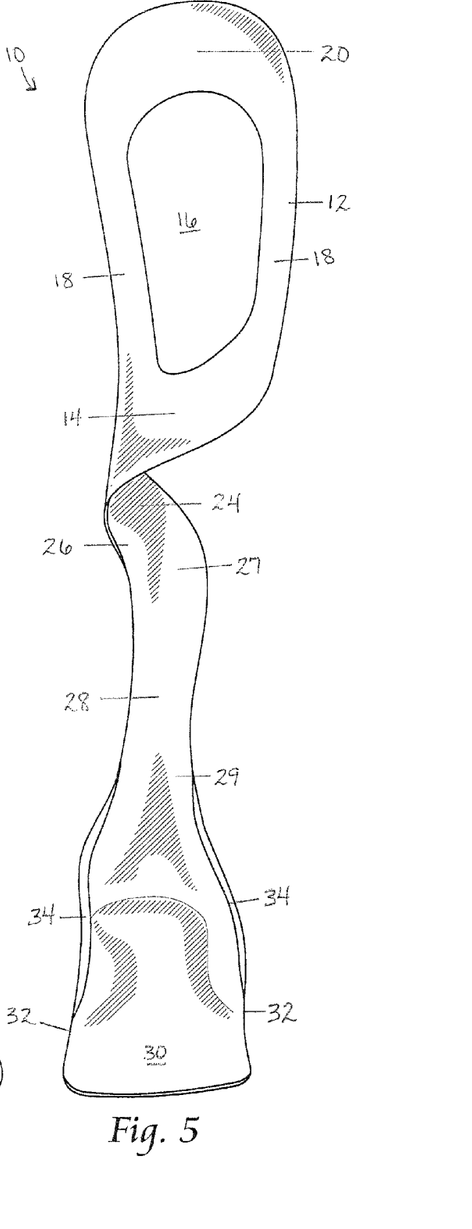
FIG. 5 is a front view of the orthosis of FIG. 1.
Figure 6:
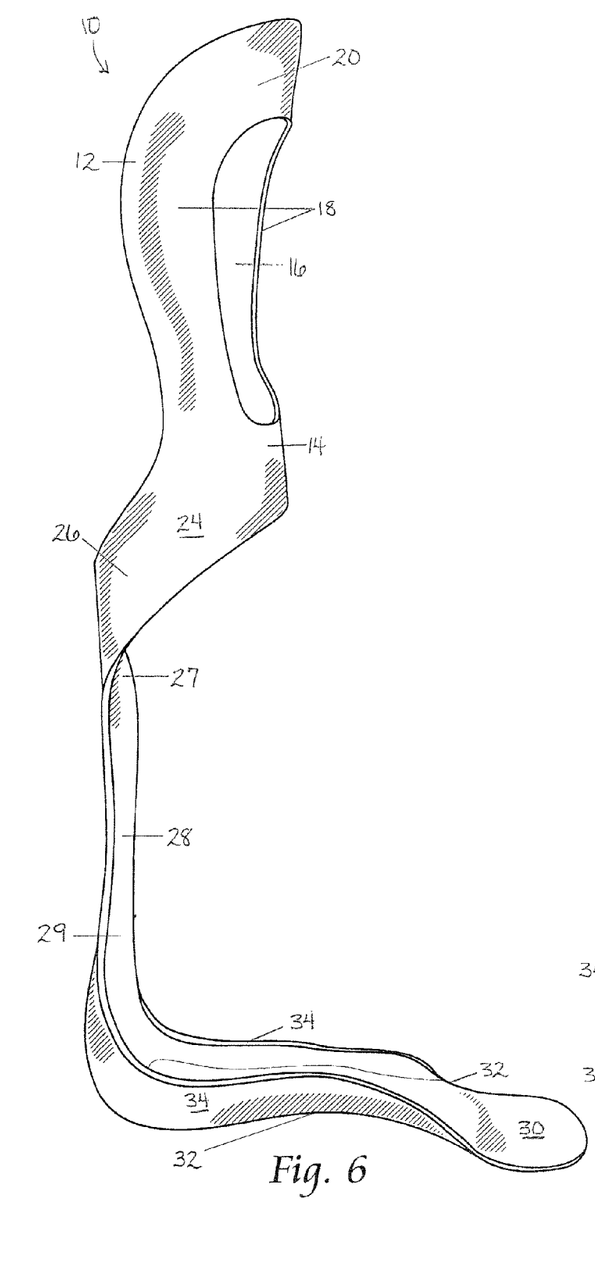
FIG. 6 is a right side view of another embodiment of an ankle foot orthosis of the present invention.
Figure 7:
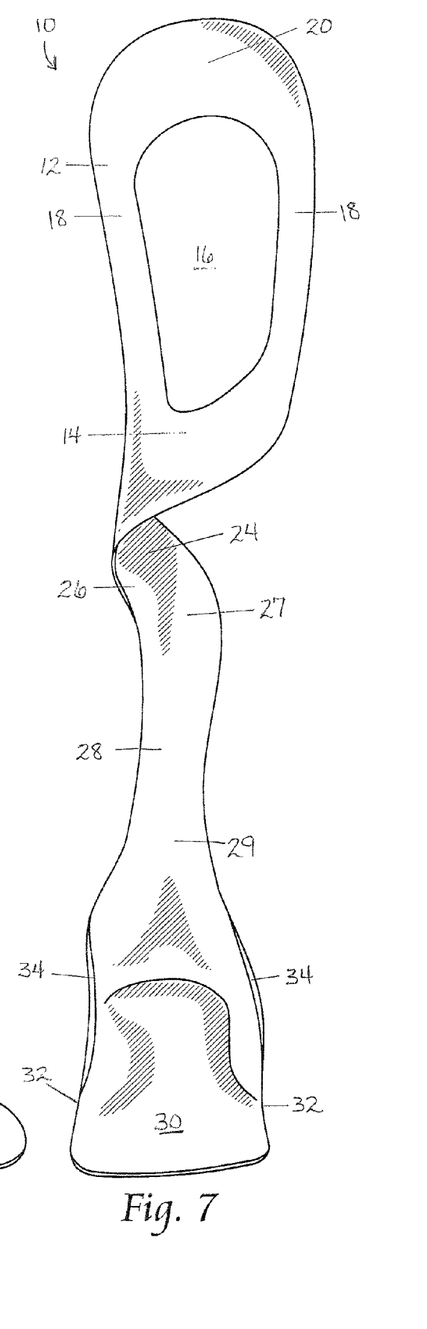
FIG. 7 is a front view of the orthosis of FIG. 6.
Figures 8, 9:
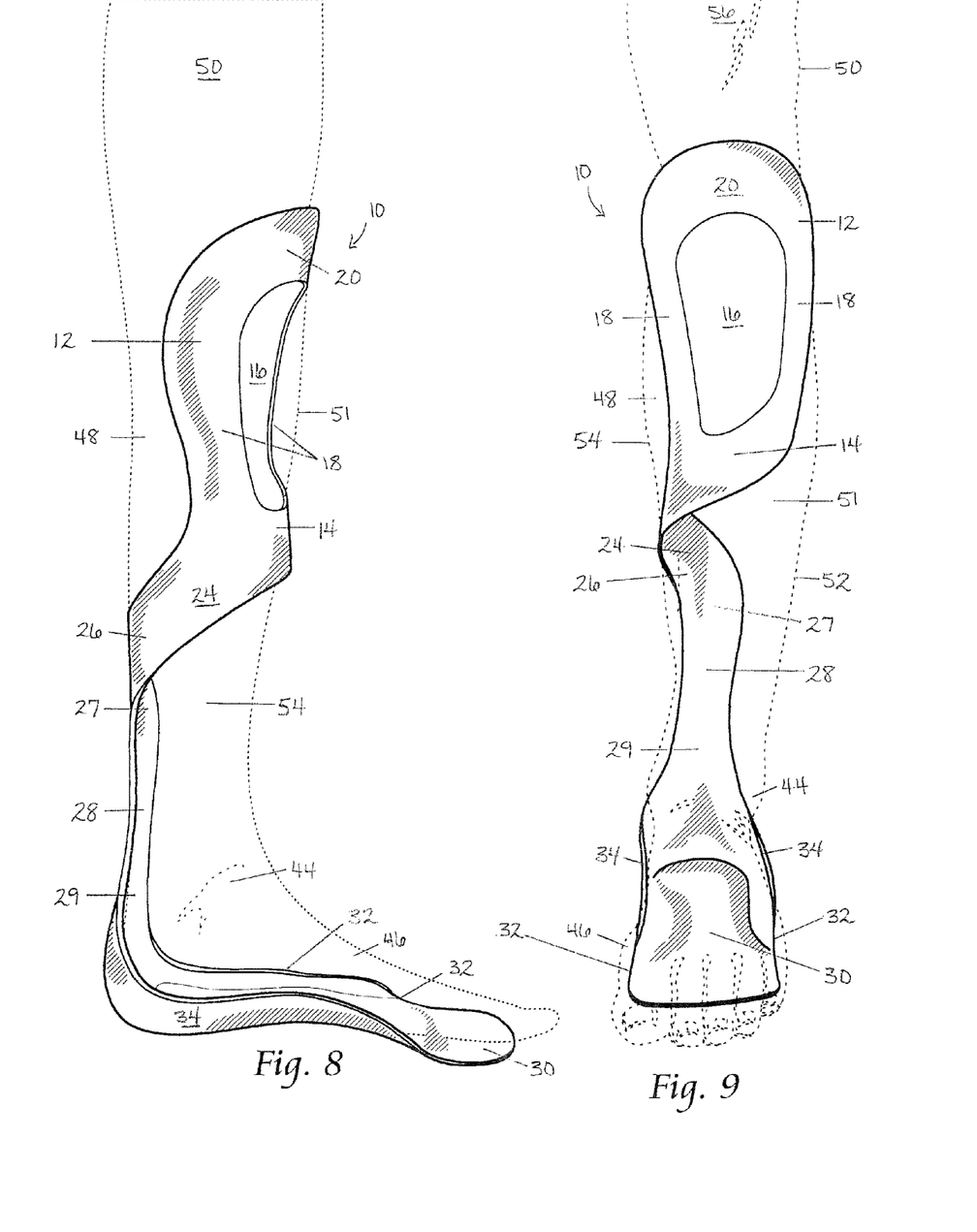
FIG. 8 is a right side view of the orthosis of FIG. 6, shown in use with a left leg drawn in phantom lines.
FIG. 9 is a front view of the orthosis of FIG. 6, shown in use with a left leg drawn in phantom lines.
Figure 10:
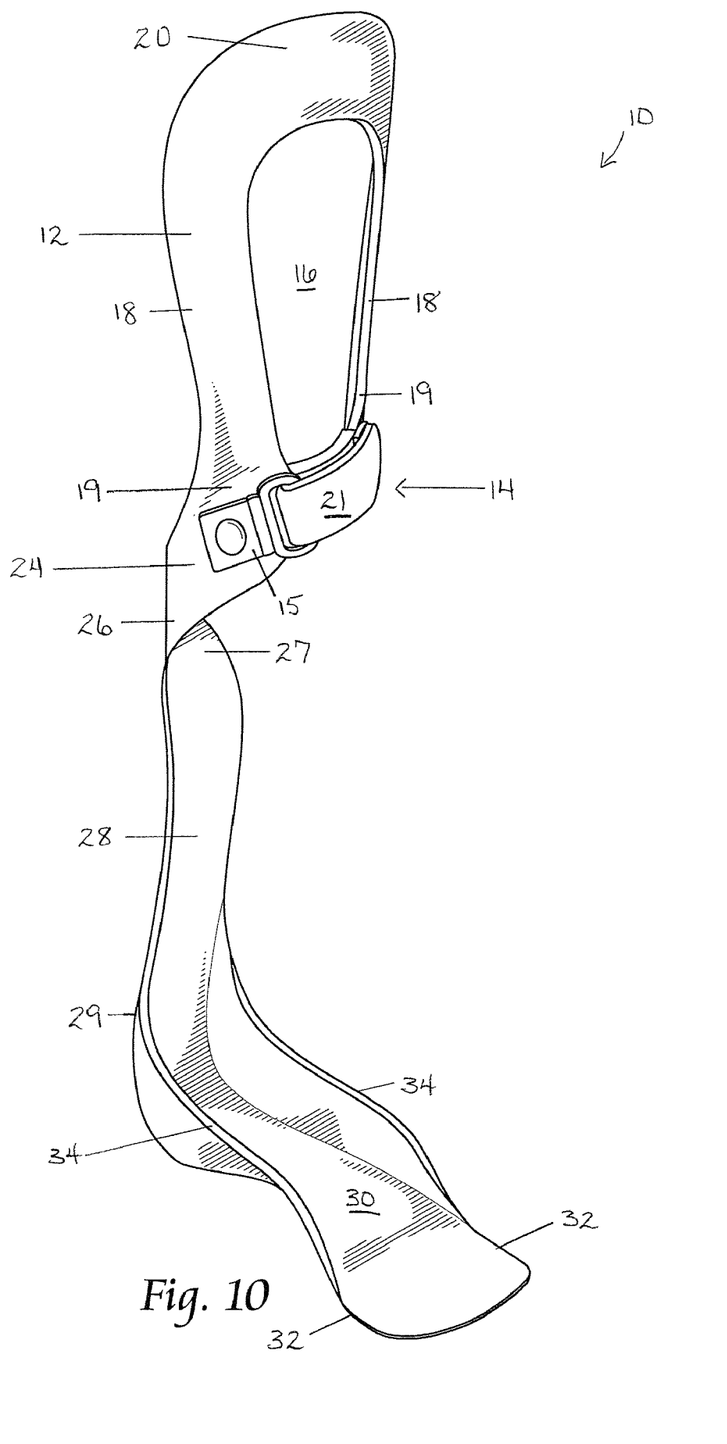
FIG. 10 is a perspective view of another embodiment of an ankle foot orthosis of the present invention, wherein the orthosis is adjustable.
Figure 11:
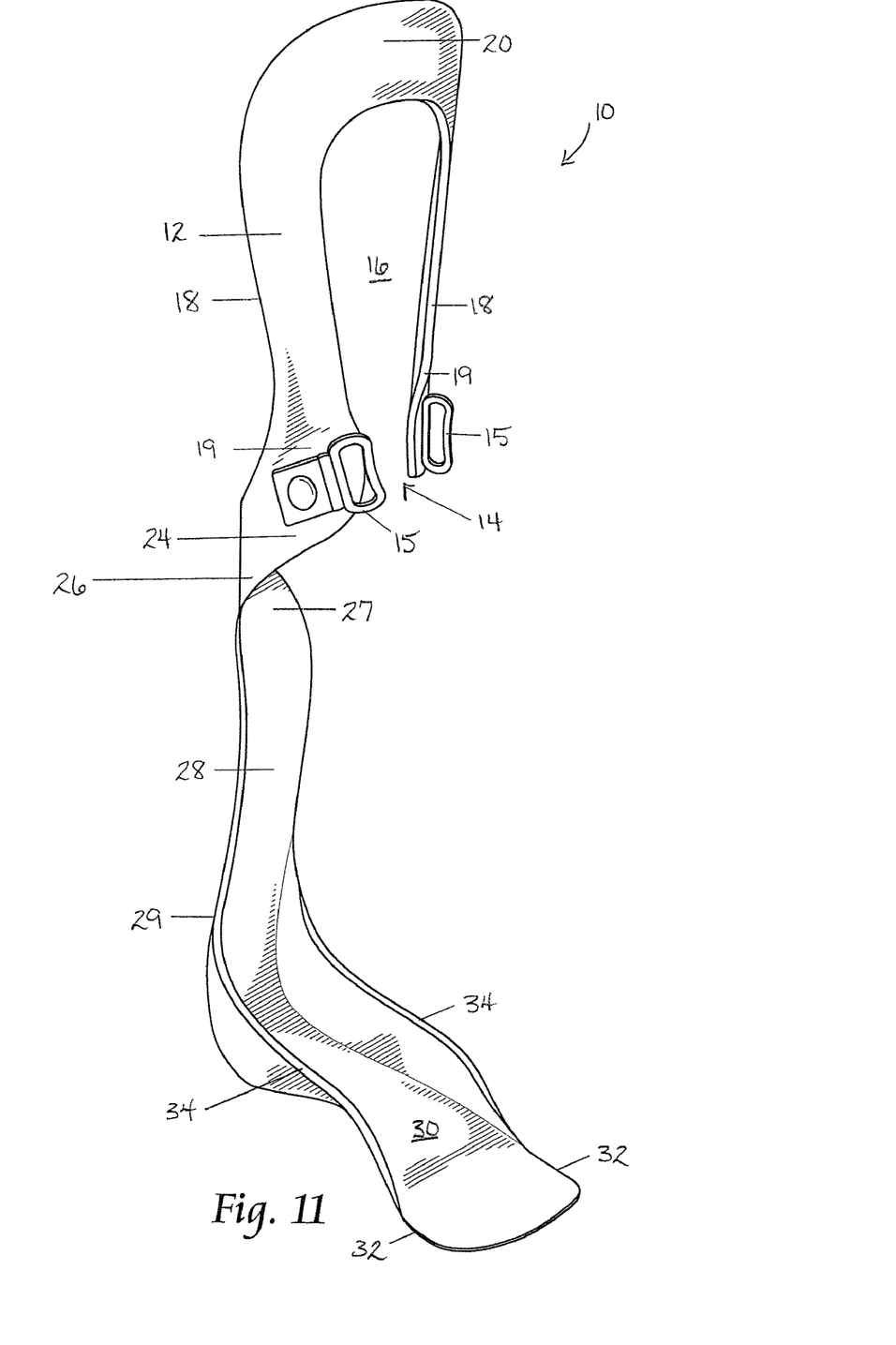
FIG. 11 is a perspective view of the orthosis of FIG. 10, shown with the adjustable strap removed.
Figure 12:
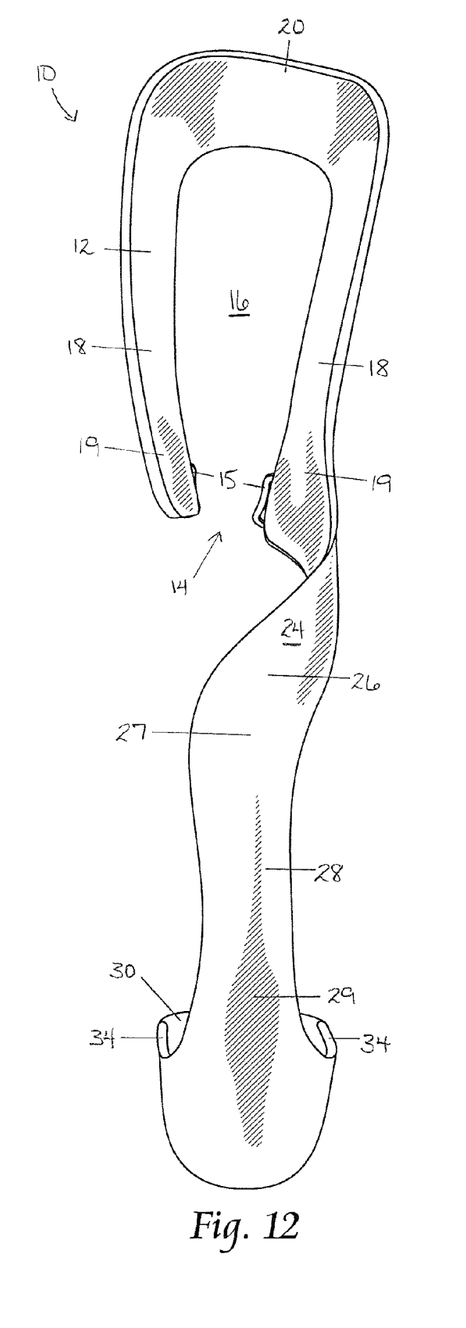
FIG. 12 is a rear view of the orthosis of FIG. 11.
Figure 13:
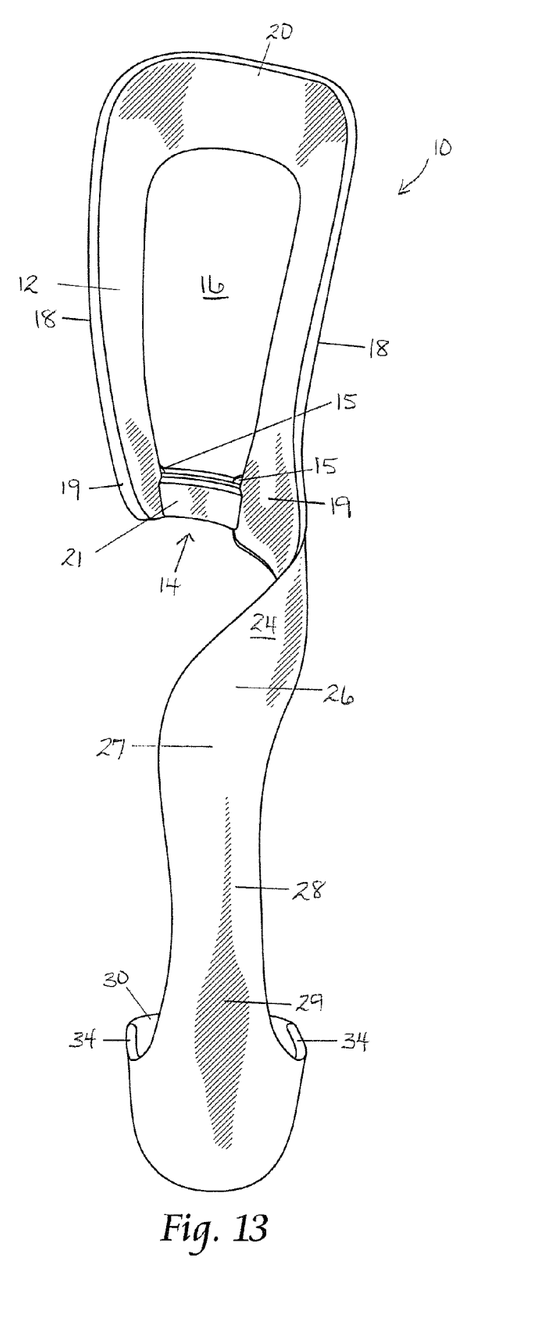
FIG. 13 is a rear view of the orthosis of FIG. 10.
Figure 14:
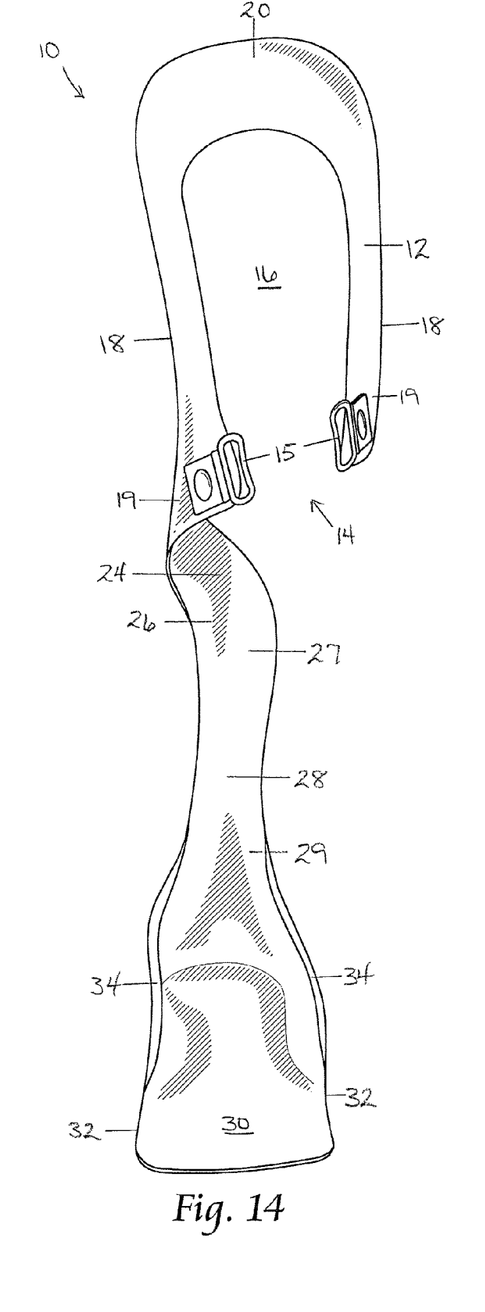
FIG. 14 is a front view of the orthosis of FIG. 11.
Figure 15:
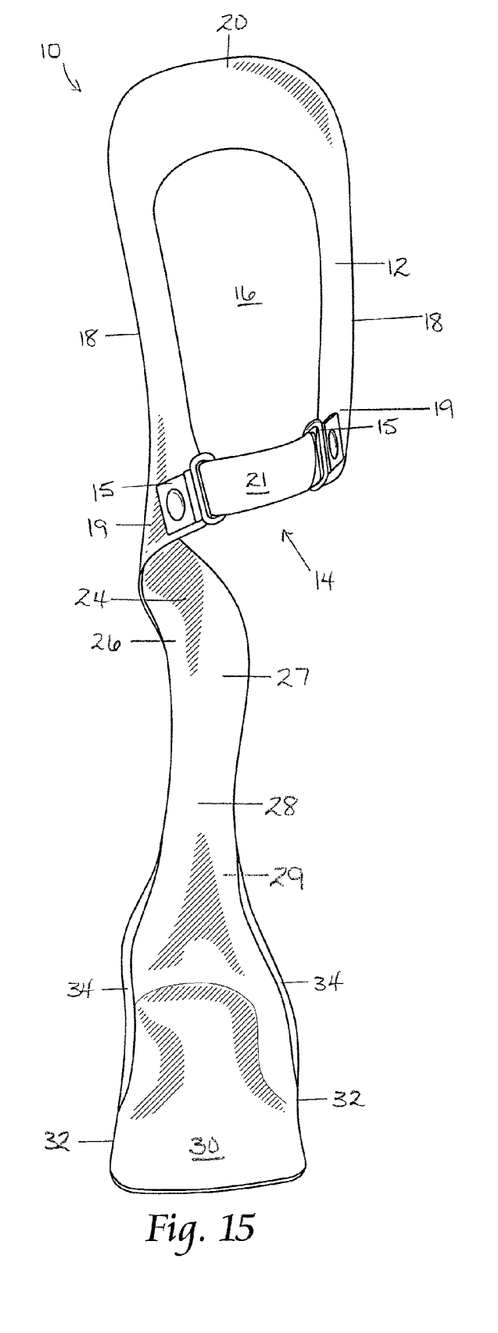
FIG. 15 is a front view of the orthosis of FIG. 10.
Figure 16:
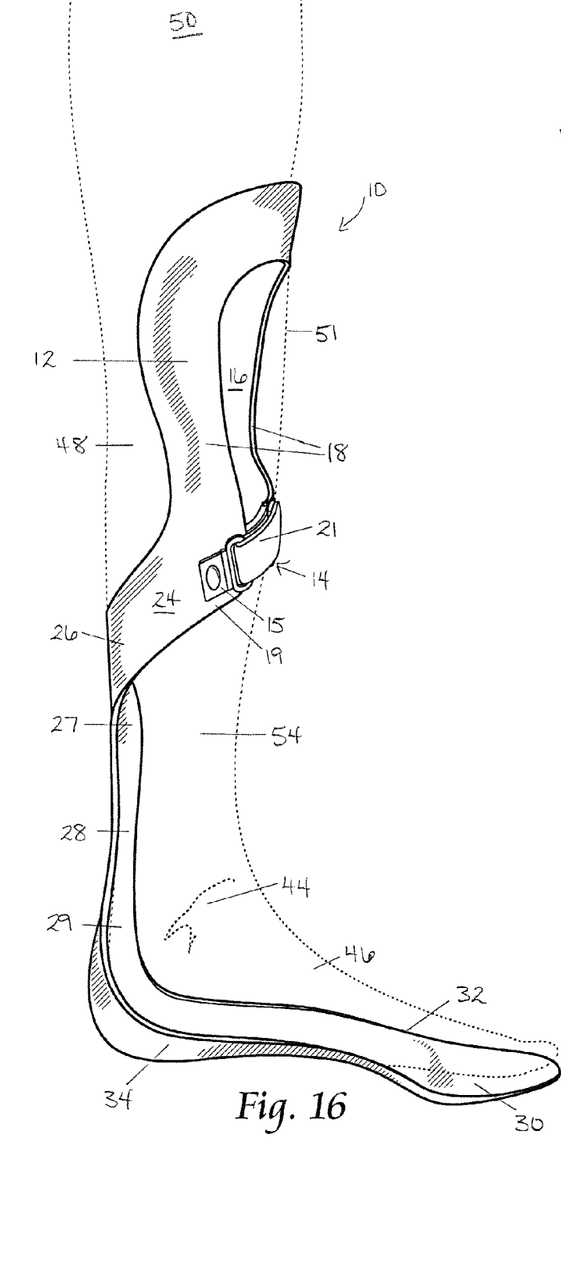
FIG. 16 is a right side view of the orthosis of FIG. 10.
Figure 17:
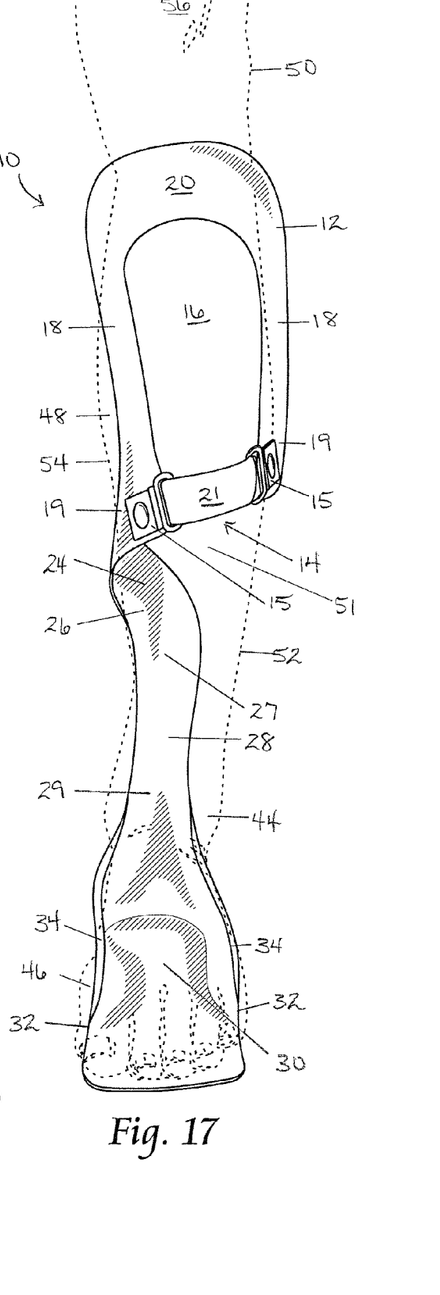
FIG. 17 is a front view of the orthosis of FIG. 10, shown in use with a left leg drawn in phantom lines.

The foot plate 30 extends perpendicularly from a distal end 29 of the rear support member 28. The foot plate 30 is shown as being flat to receive the foot 46 of the user. The foot plate 30 may be dimensioned to fit either the left foot or the right foot exclusively. Or, the foot plate 30 may be dimensioned to fit either the left foot or the right foot interchangeably. The foot plate 30 may have at least one sidewall 34 extending upwardly from a side edge 32 of the foot plate 30. The sidewall 34 may be located on either the medial or lateral part of the foot 46. Or, there may be two sidewalls 34, extending upwardly from the two side edges 32 of the foot plate 30. These sidewalls 34 help to prevent the foot 46 from moving left or right in a transverse plane. In FIG. 3, the sidewalls 34 are shown as extending higher than those shown in FIG. 6. The height of the sidewalls 34 may vary depending upon the size of the user's foot 46. It should be clearly understood that substantial benefit may also be derived from the foot plate 30 not having any sidewalls 34. This would be beneficial, for example, when the orthosis 10 is pre-made rather than being custom-made to the user's specific foot dimensions.

In addition to providing balance control, the orthosis 10 of the present invention provides a true energy storing function. The rear support member 28 and the proximal end of the foot plate 30 flex and release in a forward vector, thus helping to propel the leg 50 forward.

While the invention has been particularly shown and described with reference to preferred embodiments thereof, it will be understood by those skilled in the art that the foregoing and other changes in form and details may be made therein without departing from the spirit and scope of the invention.

I claim:

1. An ankle foot orthosis comprising:
   a concave front support member for receiving an anterior portion of a leg below a knee of a user, said front support member defining an oval aperture dimensioned to frame the anterior surface of the tibia of a user, wherein said oval aperture being formed by:
   two side portions of said front support member for providing lateral stabilization;
   a proximal end of said front support member extending from one side portion of the front support member to the other side portion of the front support member, said proximal end of said front support member for providing forward stabilization; and
   a distal end of said front support member extending from one side portion of said front support member to the other side portion of said front support member, said distal end of said front support member for providing forward stabilization and adjustability;
   a concave middle support member extending from said distal end of said front support member for receiving one of a lateral portion and a medial portion of said leg of said user;
   a rear support member extending from a distal end of said middle support member, said rear support member being dimensioned to contact the back of the calf muscle of said user; and
   a foot plate extending perpendicularly from a distal end of said rear support member.

2. The orthosis of claim 1 wherein said foot plate being dimensioned to fit a specific foot, said foot being one of a left foot and a right foot.

3. The orthosis of claim 1 wherein said foot plate being dimensioned to fit one of a left foot and a right foot interchangeably.

4. The orthosis of claim 1 wherein said foot plate having at least one sidewall extending upwardly from a side edge of said foot plate.

5. The orthosis of claim 1 wherein said foot plate having two sidewalls extending upwardly from two side edges of said foot plate.

6. The orthosis of claim 1 wherein said distal end of said front support member comprises:
   two buckles, wherein one buckle is attached to a distal end of each of said two side portions of said front support member; and
   an adjustable strap coupled to said two buckles.

7. A method for providing balance control comprising the steps of:
   providing an ankle foot orthosis comprising:
   a concave front support member for receiving an anterior portion of a leg below a knee of a user;
   a concave middle support member extending from a distal end of said front support member for receiving one of a lateral portion and a medial portion of said leg of said user;

a rear support member extending from a distal end of said middle support member for receiving a back portion of a calf muscle of said user; and a foot plate extending perpendicularly from a distal end of said rear support member;

providing lateral stabilization by side portions of said front support member;

providing forward stabilization by a proximal end and said distal end of said front support member; and providing rear stabilization by said rear support member.

8. The method of claim 7 further comprising the step of creating a force couple by providing opposing stabilization forces by said front support member and said rear support member by coupling said distal end of said front support member to a proximal end of said rear support member via said middle support member.

9. The method of claim 7 further comprising the step of providing energy storing by flexing and releasing of said rear support member in a forward vector and by flexing of a proximal end of said foot plate.

10. The method of claim 7 further comprising the step of relieving pressure on the anterior surface of a tibia by an aperture defined by said front support member.

* * * * *